United States Patent [19]

Caracciolo

[11] 4,419,189

[45] Dec. 6, 1983

[54] DISTILLATION OF 1,4-BUTANEDIOL

[75] Inventor: Vincent P. Caracciolo, Wilmington, Del.

[73] Assignee: E. I. Du Pont de Nemours & Co., Wilmington, Del.

[21] Appl. No.: 338,475

[22] Filed: Jan. 11, 1982

[51] Int. Cl.³ .......................... B01D 3/06; B01D 3/26; C07C 29/80; C07C 31/20

[52] U.S. Cl. ........................ 203/77; 203/18; 203/88; 203/DIG. 19; 568/868

[58] Field of Search ............ 203/88, 74, 77, DIG. 19, 203/99, 18, 91; 568/868

[56] References Cited

U.S. PATENT DOCUMENTS

| | | | |
|---|---|---|---|
| 2,629,686 | 2/1953 | Grosser | 202/52 |
| 2,768,214 | 10/1956 | McKinley | 260/637 |
| 2,950,326 | 8/1960 | Hort | 260/635 |
| 2,967,893 | 1/1961 | Hort | 260/635 |
| 3,852,164 | 12/1974 | Chow et al. | 203/18 |
| 3,891,511 | 6/1975 | Danneil et al. | 203/81 |
| 3,945,891 | 3/1976 | Aal et al. | 203/88 |
| 4,032,458 | 6/1977 | Cooley et al. | 568/868 |
| 4,032,583 | 6/1977 | Arganbright | 568/868 |
| 4,162,145 | 7/1979 | Alleman | 203/88 |

FOREIGN PATENT DOCUMENTS

| | | |
|---|---|---|
| 529118 | 8/1956 | Canada . |
| 1025852 | 11/1954 | Fed. Rep. of Germany . |
| 959366 | 3/1957 | Fed. Rep. of Germany . |
| 973613 | 4/1960 | Fed. Rep. of Germany . |

OTHER PUBLICATIONS

R. J. Hengstebeck: *Distillation Principles and Design Produres*, pp. 17-21; 1961.

*Primary Examiner*—Wilbur L. Bascomb, Jr.

[57] ABSTRACT

Excess water and color-forming materials present in crude 1,4-butanediol are reduced by subjecting the crude 1,4-butanediol to distillation under conditions wherein substantially all the water present in the crude 1,4-butanediol is first removed and then the 1,4-butanediol with reduced water content is further refined by flash evaporation under vacuum.

2 Claims, 1 Drawing Figure

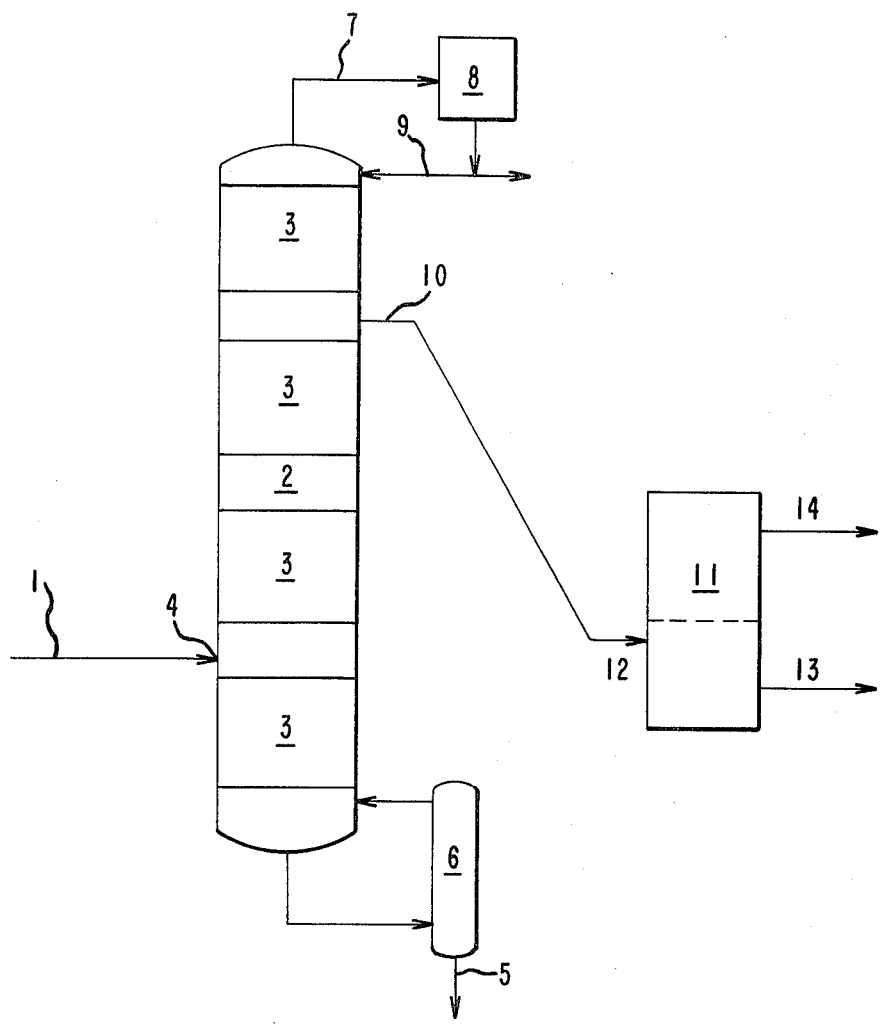

DISTILLATION OF 1,4-BUTANEDIOL

DESCRIPTION

1. Technical Field

The process of the invention relates to a method for removing excess water and color-forming materials from crude 1,4-butanediol by distillation and flash evaporation under vacuum.

2. Background Art 1,4-butanediol, hereinafter referred to as BAD, is conventionally prepared by the catalytic hydrogenation of butynediol. The crude BAD from the hydrogenation contains excess water and other impurities such as color-forming materials.

The art teaches several methods for removing water, impurities and/or color formers from BAD, e.g., U.S. Pat. Nos. 2,629,686; 2,768,214; 3,852,164 and 3,891,511. However, the above methods either do not remove enough water, impurities, and/or color-forming materials present to provide the desired product or involve complicated and expensive routes for their removal.

DISCLOSURE OF THE INVENTION

Now it has been found that excess unessential water and color-forming materials, or their precursors, present in crude BAD can be reduced more efficiently by subjecting the crude BAD to distillation under conditions wherein substantially all of the water present in the crude BAD is first removed and then the BAD with reduced water content is further refined at lower pressure by flash evaporation to sufficiently remove remaining water to provide a specification grade product.

Crude BAD contains 1-20% by weight water and organic impurities that boil lower than BAD, 0.05-5% by weight of high boiling organic tars and inorganic salts, and 80-99% BAD.

In an embodiment of the invention crude BAD containing approximately 5% by weight water is fed to a column containing packed sections or trays at a midpoint or lower but not below the packing. Preferably crude BAD is fed to a column containing four packed sections at a point one packed section above the bottom.

If the column is filled with packing, many conventional types of packing can be employed, e.g., Koch Sulzer type mesh packing or stainless steel Pall rings. In some embodiments it may be desirable to use actual trays or a mixture of trays and packing. In a preferred embodiment the upper part of the column will be packing while the lower part will be trays with the feed of crude BAD being introduced into the tray portion.

The column is operated at a vacuum low enough to maintain reboiler temperature below ~175° C. At a point on the distillation column above the point where the feed is introduced into the column and below the top of the packing or trays, a liquid stream is removed that comprises BAD with substantially reduced water content relative to the feed, i.e., by substantially reduced is meant less than 5000 ppm, preferably less than 1500 ppm. The side draw BAD stream, substantially free of undesirable quantities of color formers, but still containing an excess of unessential water is fed to a flash evaporator below the liquid level to give the feed a chance to equilibrate with the flasher liquid. The flash evaporator is maintained under a higher vacuum than that of the column. There sufficient material is flashed overhead (~7% of the product draw) using the sensible heat content of the stream. A refined BAD containing <400 ppm water is removed from the bottom of the flasher.

High boiling organic tars and inorganic salts are removed from the bottom of the distillation column or from a reboiler as a liquid purge. Low boiling organic impurities and water are removed from the top of the distillation column, condensed and a portion fed back as reflux while the rest is purged. The amount of reflux is not critical and can vary from a ratio of 1:1 to 5:1.

The operation of the distillation column can be adjusted using conventional techniques to obtain a desired water content. The column is preferably operated under vacuum so that the temperature of distillation does not exceed 175° C., i.e., the maximum base temperature. At temperatures above 175° C. BAD tends to decompose into tetrahydrofuran and water. Thus, the column is usually operated under 200 mm Hg and preferably 60-100 mm Hg at the top and 120 mm Hg at the bottom.

The removal of the BAD stream from the distillation column at a point above the midpoint, i.e., above the feed, but below the packing top level is important. Any removals above the packing will be in the form of vapors containing much larger amounts of water. As the point of removal of the BAD stream approaches the point at which the crude BAD is fed, the amount of water present in the BAD stream increases. However, as long as the stream is removed above the feed level, its water content will be substantially reduced. The stream removed from the distillation column with reduced water content and sent to the vacuum flasher is water white in appearance.

The range for withdrawing liquid BAD from the distillation column is where the water content is from 0-5000 ppm, preferably below 2000 ppm and most preferred below 1500 ppm, irregardless of the water concentration in the crude BAD. It was found that the relative volatility of color formers out of BAD goes from 0.63 to 1.0 as the water is increased to 5000 ppm. Thus, the relative volatility indicates the substantially more ready removal of color formers out of BAD at 0.63 as compared to 1.0.

The FIGURE is a flow drawing illustrating an embodiment within the scope of the process of the invention.

Referring now to the drawing crude, BAD 1 is fed into distillation column 2 containing four sections of packing 3 of stainless steel Pall rings at a point 4 above the bottom packed section 3. High boiling organic tars 5 are removed from the bottom of the column through reboiler 6 and low boiling organic impurities and water 7 are removed from the top of the column, condensed 8, and part refluxed 9 to the column and part purged. A liquid stream 10 is removed below the top packed section of the column and sent to vacuum flasher 11 at a point 12 below the liquid level within the flasher. A product stream 13 is removed as a bottom stream from the flasher with reduced water content. Water, low boiling organic impurities and some BAD 14 are removed from the top of the flasher.

The invention is further illustrated by the following example wherein all percentages or parts are by weight unless otherwise indicated.

EXAMPLE A (SINGLE-COLUMN DISTILLATION SIMULATION)

A three-step simulation of side draw distillation followed by flashing to remove excess water was done as follows:

Step 1: Low Boiler Removal

BAD crude containing 4.7 wt % water was fed at 6.4 g/min to the reboiler of a 5 sieve plate, 1 inch Oldershaw column. The column was operated at a head pressure of 65 MM Hg absolute using a reflux ration of 4.5/1 and an overheads takeoff of 1.3 g/min to remove the bulk of the water and other low boilers to simulate the distillation operation above the point of product draw-off.

Step 2: High Boiler Removal

The bottoms product from Step 1 which still contained high boilers was fed at 4.8 g/min to a 15 sieve plate, 1 inch Oldershaw column above the 5th plate to simulate the distillation operation up to the point of product draw-off. The column was operated at a head pressure of 65 MM Hg absolute at a reflux ratio of 1.2/1. The refined product was taken off overhead at 4.1 g/min giving a water white product containing 2500 ppm water and polyester with APHA color of 115.

Step 3: Water Removal by Flashing

The product from Step 2 containing 2500 ppm water was fed below the liquid level to an electrically heated flasher at a fed rate of 7.6 g/min. The flasher was operated at a pressure of 25 MM Hg absolute at a pot temperature of 139° C. The water containing overheads were drawn off at 0.56 g/min (~7% of the feed). The refined BAD product withdrawn from the flasher contained 355 ppm water with a BAD content of 9979 wt % compared to a typical refined BAD product of ≦400 ppm water and 99.75 wt % BAD obtained by more costly methods described in the art.

EXAMPLE B

Refined BAD to which water was added to simulate liquid product removed from the distillation column was fed to a vacuum flasher to demonstrate that the excess water was readily reduced to <400 ppm by flashing. The results are summarized below.

| BAD Feed Water Content, ppm | Flasher Pressure, MM Hg Absolute | Flasher Temp., °C. | Wt % of Feed Flashed | Bottoms Product Water Content, ppm |
|---|---|---|---|---|
| 1500 | 25 | 139 | 7.1 | 210 |
| 1600 | 25 | 137 | 6.5 | 250 |
| 2500 | 25 | 139 | 7.3 | 360 |
| 2300 | 25 | 139 | 5.1 | 460 |
| 1400 | 72 | 164 | 11.2 | 180 |
| 1450 | 72 | 163 | 6.6 | 250 |
| 2400 | 72 | 162 | 10.0 | 260 |

Current refining technique requires the use of two columns to achieve the same quality. The proposed single column-flasher combination will produce the required purity at lower investment and will utilize the heat content of the side stream to flash off the water, thus reducing energy consumption. An ultra pure product can be obtained by reprocessing the product through the equipment on a campaign basis or possibly by increasing column reflux ratio and reducing the feed rate to produce a higher purity at a lower production rate when needed.

The color formers removed by the process of the invention are compounds that color the polyester product from the reaction of BAD and an appropriate dibasic acid. They are measured by first preparing a polyester with BAD and then following the test procedure described as ASTM D 1209 to measure the color. There is a relative reduction of color in the polyester product when the color formers are removed from BAD by the process of the invention.

POLYESTER TEST METHOD 90 g of 1,4-butanediol and 104 g of adipic acid are charged to a 3 necked 500 ml RB flask equipped with a thermometer, distillation head, magnetic stirrer and a heating mantle. The system is evacuated and filled with $N_2$ three times and left under a slow $N_2$ flush. The flask is heated to 180° C. ($N_2$ flush is turned off when temperature reaches 140° C.), and is maintained at 180° C. for 7 hours. The resulting polyester is cooled to about 100° C. and the APHA color is measured by comparison with platinum cobalt standards with an appropriate colorimeter.

I claim:

1. A continuous two-stage process for refining 1,4-butanediol containing 1–20% by weight of water and 0.05–5% by weight of tars, the process comprising
   (a) in the first stage, passing the butanediol to a column at its midpoint or below, subjecting the 1,4-butanediol to vacuum distillation, and withdrawing partially refined liquid butanediol from the column at a point above its entry point, and
   (b) in the second stage, subjecting the butanediol from the first stage to a single-stage flash evaporation under a vacuum greater than that in the column of the first stage, and withdrawing the refined butanediol, which contains less than 400 ppm of water and is substantially free of color-formers, from the evaporation stage as the unvaporized component.

2. The process of claim 1 in which the vacuum in the first stage column is maintained at 200 mm of Hg or less.

* * * * *